(12) United States Patent
Gray

(10) Patent No.: US 7,503,694 B2
(45) Date of Patent: Mar. 17, 2009

(54) DENTAL IMAGE QUALITY AND DOSE ANALYZER

(76) Inventor: Joel E. Gray, 222 Lakview Ct., Steger, IL (US) 60475

( * ) Notice: Subject to any disclaimer, the term of this patent is extended or adjusted under 35 U.S.C. 154(b) by 164 days.

(21) Appl. No.: 11/699,858

(22) Filed: Jan. 30, 2007

(65) Prior Publication Data

US 2007/0183590 A1    Aug. 9, 2007

Related U.S. Application Data

(60) Provisional application No. 60/771,604, filed on Feb. 8, 2006.

(51) Int. Cl.
*G01D 18/00* (2006.01)
(52) U.S. Cl. ........................ 378/207; 378/204
(58) Field of Classification Search ............... 378/108, 378/207, 38–40, 98.8, 204
See application file for complete search history.

(56) References Cited

U.S. PATENT DOCUMENTS

| | | | |
|---|---|---|---|
| 3,612,870 A | 10/1971 | Brennan | 250/473.1 |
| 5,493,600 A | 2/1996 | Jacobson | 378/207 |
| 5,506,884 A * | 4/1996 | Goodenough et al. | 378/207 |
| 5,651,046 A | 7/1997 | Floyd et al. | 378/207 |
| 5,841,835 A | 11/1998 | Aufrichtig et al. | 378/207 |
| 6,127,685 A | 10/2000 | Yoder et al. | 250/472.1 |
| 6,198,108 B1 | 3/2001 | Schweitzer et al. | 250/472.1 |
| 6,259,112 B1 | 7/2001 | Lim | 250/581 |
| 6,454,460 B1 | 9/2002 | Ramanathan et al. | 378/207 |
| 6,553,095 B2 | 4/2003 | Rinaldi et al. | 378/108 |
| 6,694,047 B1 | 2/2004 | Farrokhnia et al. | 382/132 |

OTHER PUBLICATIONS

Landauer, "Luxel® + Dosimeter for X, Gamma, Beta, and Neutron Radiation," Landauer, Inc., 2 Science Road, Glenwood, IL, 60425, 708-755-7000, www.landauerinc.com, 2005, 1 page.
International Search Report from PCT International Application No. PCT/US2007/002630 dated Oct. 25, 2007 (2 pages).

* cited by examiner

*Primary Examiner*—Courtney Thomas
(74) *Attorney, Agent, or Firm*—Brinks Hofer Gilson & Lione

(57) ABSTRACT

A device and method for evaluating the performance of X-ray machines used to produce radiographic images is described. An analyzer including an X-ray dosimeter and an imaging device is sent to the facility having the X-ray machine to be evaluated. The analyzer may be used with a film pack or a digital image detector. The analyzer is exposed in accordance with testing instructions and returned to an evaluation agency. The radiation dose and HVL is determined from the dosimeter, and the image quality is determined from analysis of a radiograph of a target having differing X-ray absorption portions. A data base of results may be used to provide comparative analysis.

50 Claims, 7 Drawing Sheets

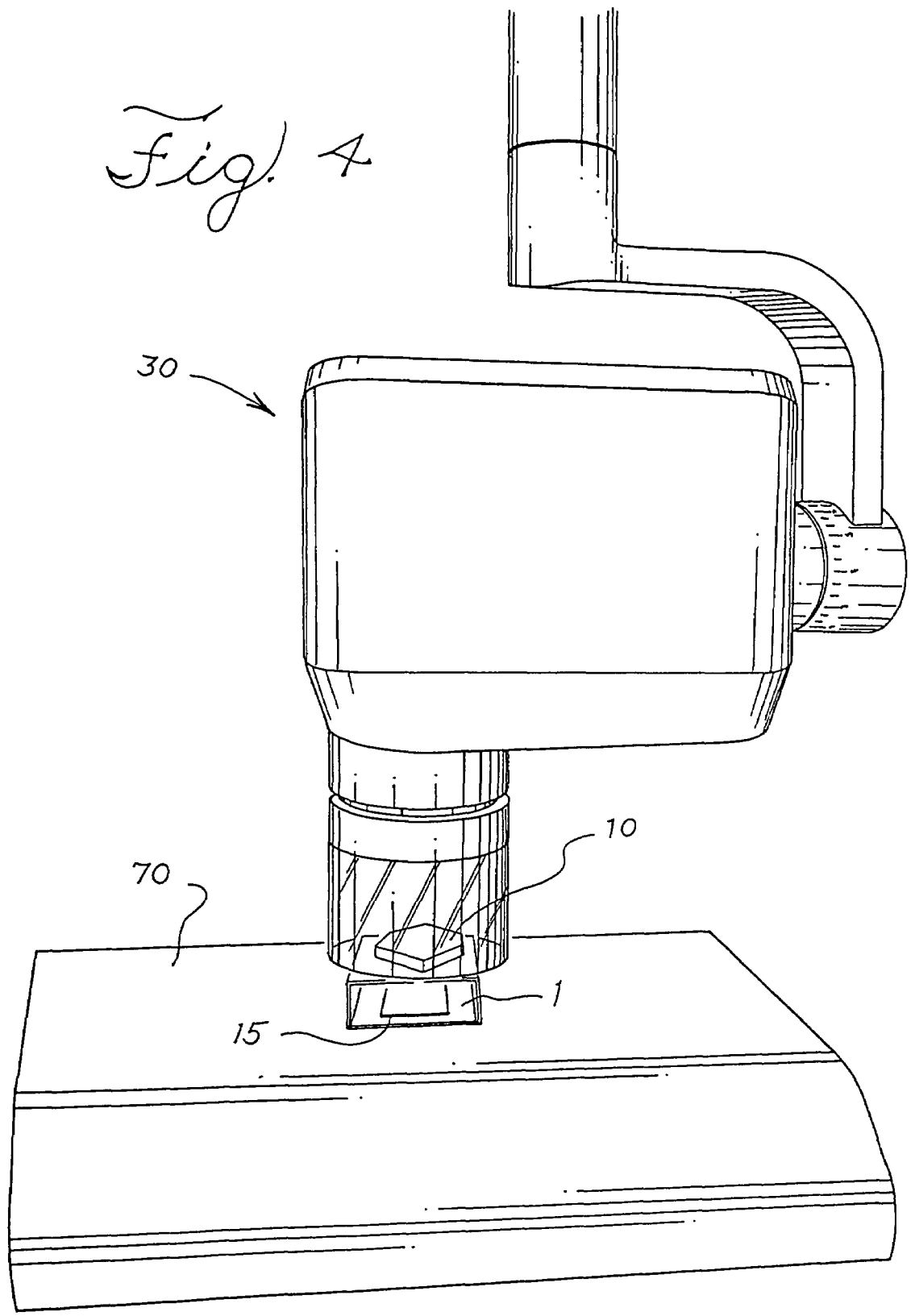

Fig. 6
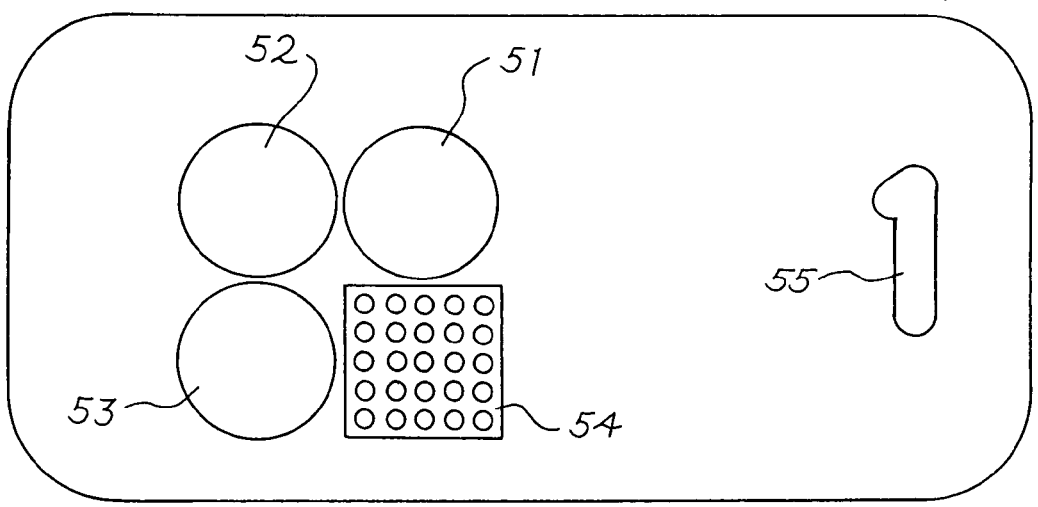
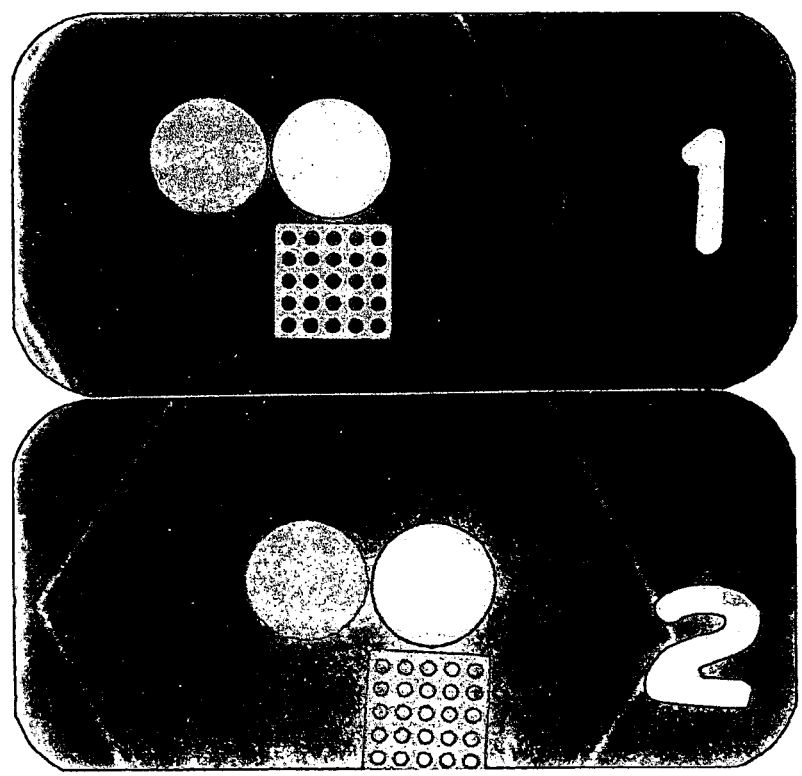
Fig. 7

DENTAL IMAGE QUALITY AND DOSE ANALYZER

This application claims the benefit of U.S. provisional application No. 60/771,604, filed on Feb. 8, 2006, which is incorporated herein by reference.

TECHNICAL FIELD

The present application relates to a device used for the evaluation of the quality of X-ray images and the radiation dose in medical, dental, or other X-ray devices, and a method of using the device so as to evaluate the quality of the X-ray film processing performed by a facility.

BACKGROUND

X-ray technology has been used to improve the quality of medical and dental diagnosis and care; however, there are known dangers in the exposure of humans and animals to ionizing radiation such as is used in X-ray imaging. A large number of independently operated facilities, such as dental offices, use X-ray technology in routine diagnosis and treatment of medical conditions and in delivering dental care to patients. The use of an X-ray device to identify areas of tooth decay, abscess, and other pathology results in a substantial portion of the population being routinely exposed to ionizing radiation, in addition to that which naturally occurs in the ambient background.

The amount of X-ray exposure or dose delivered to patient tissue during an X-ray examination varies widely with the type of images being obtained, the age and specific model of the equipment being used, and both the skill and judgment of the practitioner. Further, an X-ray device may operate such that the expected dose is not properly calibrated, or other aspects of the device such as the quality of beam collimation or beam energy may deviate from acceptable limits. Generally there are regulations, which vary in detail from state-to-state in the United States, and from country to country, as to the frequency and methods of testing of such devices. The equipment needed for such testing is generally quite sophisticated and specialized and operated by a person specifically trained in the use thereof. As such, the frequency with which each of the facilities in a jurisdiction is tested tends to be low, often with a period of years separating successive tests.

Where X-ray film is used to record the X-ray image, the image quality also depends on the image developing technique used at the facility, the quality and freshness of the chemical solution used, and the training and work habits of the personnel. Image quality may be characterized by the sharpness and contrast of the images, and inadequate imaging quality may result in misdiagnosis or the need to take additional images, thus increasing the overall patient radiation dose.

SUMMARY

A device and for evaluating the image quality and radiation dose delivered by an X-ray device and any associated film processing equipment is described.

A device for measuring the dose and image quality of an X-ray machine includes a radiation dosimeter, and a target having a test pattern. The dosimeter and the target are disposable such that the dosimeter and the target are positioned at approximately the same distance from a location suitable for placement of an image receptor. The image receptor may be included with the device or may be inserted into the device by the user.

A method of determining X-ray machine image quality and dose may include the steps of sending a dental image quality and dose analyzer to a facility having an X-ray machine to be evaluated; receiving an exposed analyzer from the facility; determining the dose received by the dosimeter; and analyzing the radiographic image obtained by exposing the analyzer.

In another aspect, a method of determining dental x-ray machine image quality and dose may include the steps of receiving a dental image quality and dose analyzer; positioning the analyzer with respect to an X-ray machine to be tested; exposing the analyzer to X-rays; and returning the analyzer to a testing laboratory.

DETAILED DESCRIPTION OF THE DRAWINGS

FIG. 4 illustrates the relationships of an X-ray machine, the dental image quality and dose analyzer and a support structure during a test exposure;

FIG. 6 is a radiograph showing the effect of the target features on the developed film gray scale; and FIG. 7 compares two radiographs taken on different X-ray machines and having different image qualities.

DESCRIPTION

Exemplary embodiments may be better understood with reference to the drawings, but these examples are not intended to be of a limiting nature. Like numbered elements in the same or different drawings perform the same or equivalent functions.

The image quality (image sharpness and quality of photographic images and film processing, or digital images) of dental radiographs and the radiation dose to the patient may be determined using a survey kit sent to the X-ray facility. Such a survey may either be voluntary, or may be required by regulation or law. As the frequency of testing, the place and method of evaluation of the resultant exposed analysis materials, and the consequences of the testing may vary from political-jurisdiction-to-political-jurisdiction, the specific aspects of the device and the process are likely to vary. However, the general from of the device and the method of use is expected to be suitable for a variety of regulatory regimes.

Figure 1A:
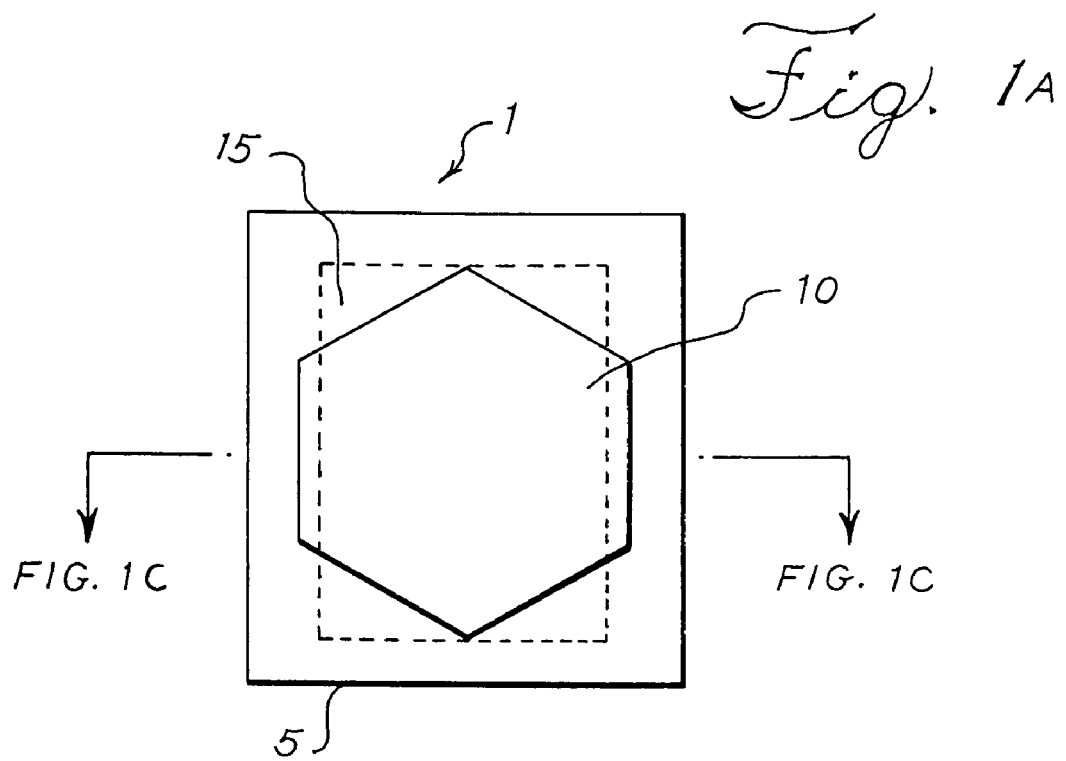
FIG. 1 is an example of a dental image quality and dose analyzer shown in: (A) plan view form the top; (B) side view of an open side; and (C) cross-sectional view.
Figure 1B:
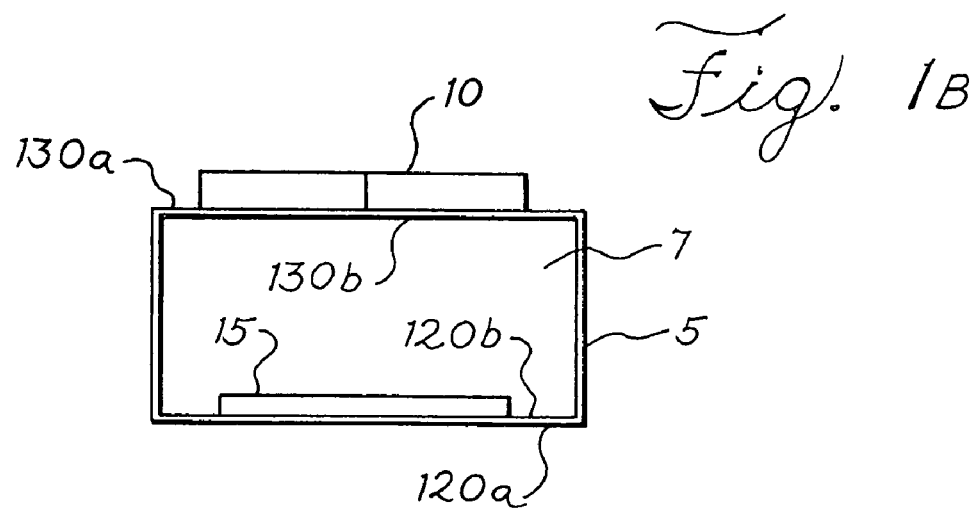

In an example, a Dental Image Quality and Dose (DI-QUAD) analyzer 1 is shown in FIG. 1. A mounting frame made of paper, plastic or other substantially X-ray-transparent material is provided, and may be formed into a rigid or foldable mounting 5. An X-ray dosimeter 10 may be mounted to one surface thereof, and one or more film packets 15 or an image receptor may be mounted to another surface such that, in operation, a film pack 15 is displaced a pre-determined distance D from the X-ray dosimeter 10. An X-ray test target (not shown) may be mounted in, or close to, the dosimeter 10.

Figure 1C:
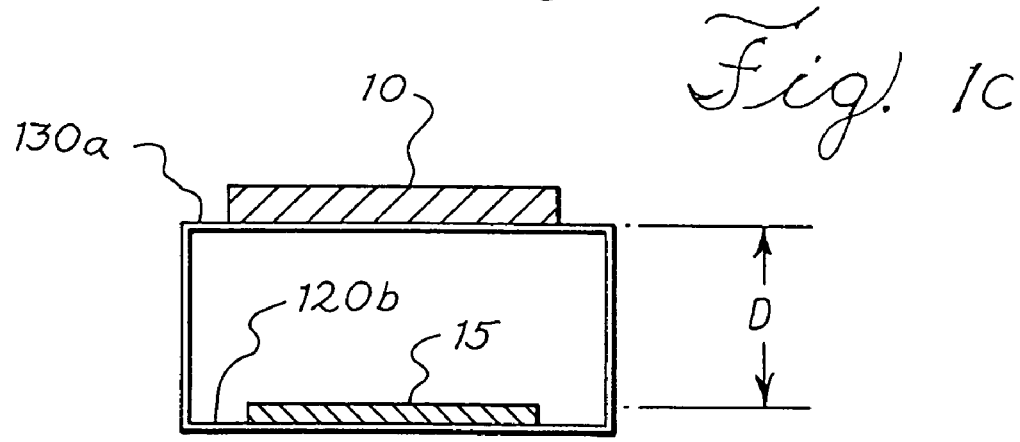

Herein, the term DIQUAD may used as a trademark for a device for performing dental image quality and dose analysis, but this is not meant to limit the device to a specific product, such as that produced and sold by DIQUAD, LLC, or to the application of the apparatus or method to dental X-ray machines. The term image receptor is used to encompass any material or device sensitive to the X-radiation and capable of producing a latent or real-time rendering of the intensity of X-radiation impinging on a surface thereof. The latent images may be developed such as by developing a photographic film, activation of a surface by laser light, or any equivalent technique that may subsequently be developed. The sensitivity may produce optical or electrical signals proportional to the X-radiation intensity and which may be converted to a form suitable for recording in analog or digital format, or interfacable to a computer having a memory circuit or other storage device. Herein, an example using one type of image receptor is not intended to exclude the use of any of the other types of image receptor As shown in FIG. 1C, showing a cross-section the analyzer 1, the film packet 15 may be mounted to an inner lower surface 120b, while the dosimeter 10 is mounted to an upper outer surface 130a so that a separation distance D is formed when the mounting is in a state where the cross-sectional area is a rectangle. In the arrangement of FIG. 1, the interior of the mounting is hollow.

Figure 2A:
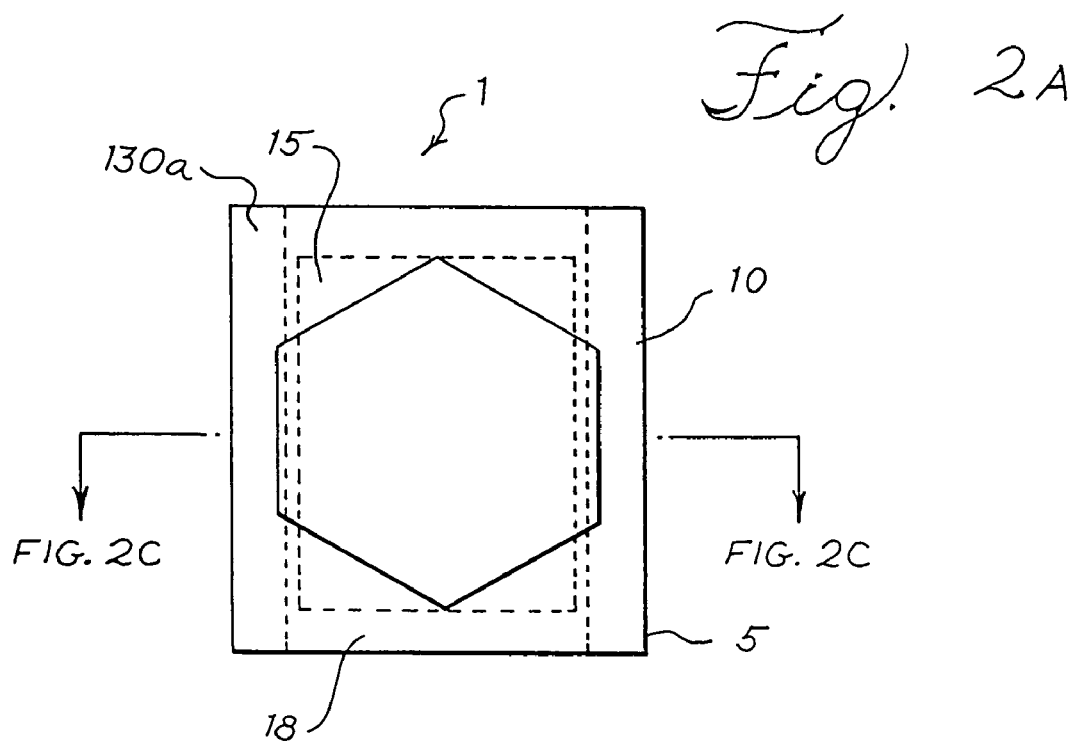
FIG. 2 is another example of a dental image quality and dose analyzer shown in: (A) plan view form the top; (B) side view of a side having a slot; and (C) cross-sectional view.

Alternatively, the housing 5 may be fabricated from a material such as a resin or other plastic or low density material having a minimal absorption coefficient for X-rays. As shown in FIG. 2A, the dosimeter is mounted to an upper outer surface 130a of the housing 5. An aperture 18 is formed in the body of the housing, the aperture being sized and dimensioned so as to receive a film packet 15 and to position the film packet 15 underneath the dosimeter 10, spaced apart therefrom by a distance D. The aperture 18 may extend entirely from one side of the body of the housing to the other side thereof, or may be arranged so that the aperture 18 can be accessed from only one side of the housing.

The analyzer 1 may be used in a method of surveying a group of facilities having dental radiographic equipment where the individual X-ray machine and facility results are compared with pre-established standards to determine whether the facility is in conformance with the standards. Alternatively, the results may be compared with a historical data base of comparable facilities and used to counsel the operator as to the quality of the images and to suggest improvements in technique.

An X-ray test target (not shown) may be provided as part of the X-ray dosimeter 10, or be mounted above or below the X-ray dosimeter 10, and may have one or more areas of differing X-ray absorption, which may be a mesh or other pattern. In use, the analyzer 1 is placed on a surface and the X-ray device to be evaluated is positioned a known distance from the X-ray dosimeter 10 of the analyzer 1.

Figure 3:
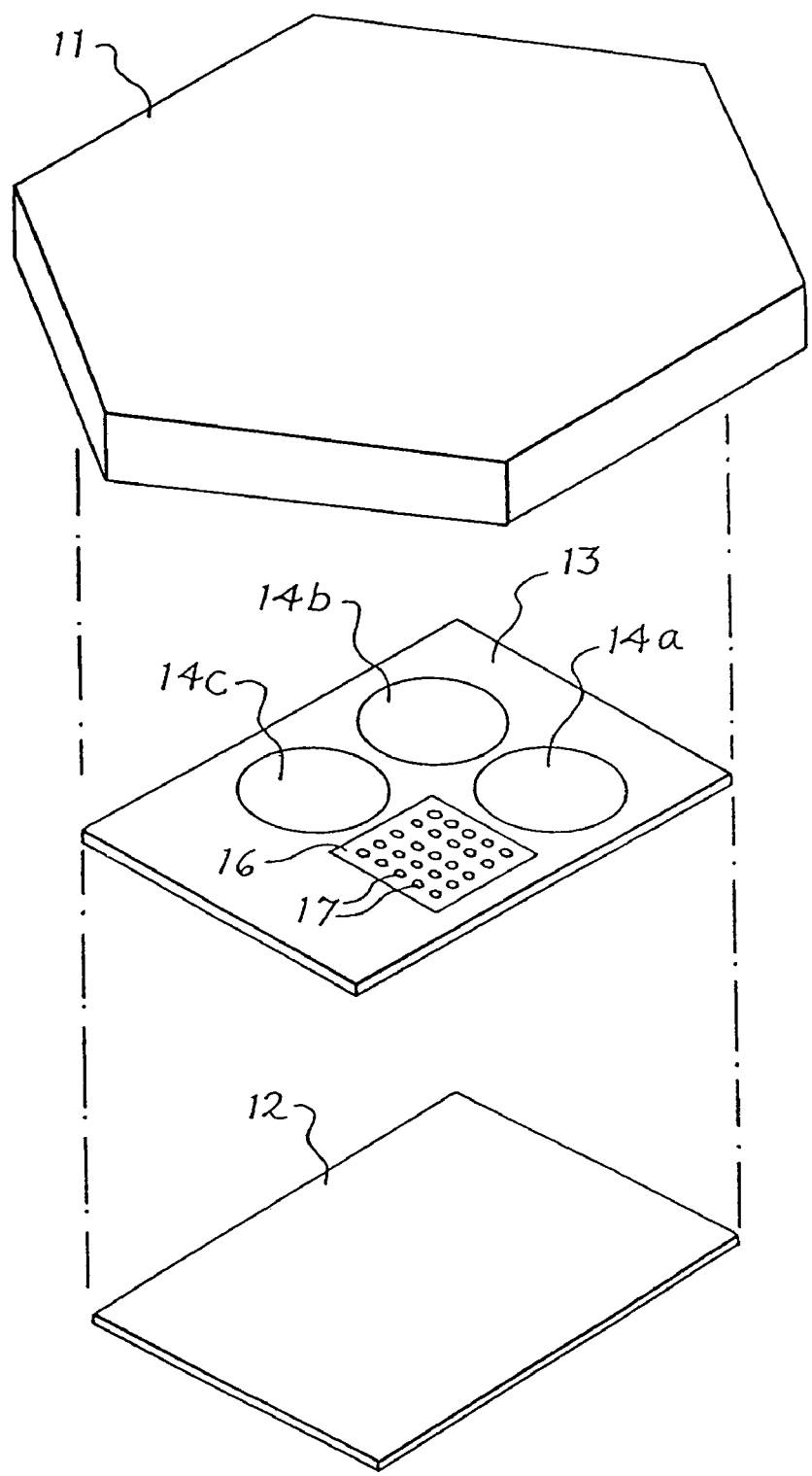
FIG. 3 is an exploded perspective view of the dosimeter including an X-ray test target.

The dosimeter 10 may be comprised of a housing 11 having a radiation sensing element 12 contained therein. As shown in the exploded view of FIG. 3, the radiation sensing element 12 may be located in proximity to an X-ray test target 13. The target 13 may be fabricated of materials having a known and controllable X-ray absorption coefficient. Areas of the target 13 are formed with differing overall absorption values for X-rays penetrating the target 13 orthogonal to the flat surface thereof. A group of targets 14a-c may have a wide range of absorption values which may range from approximately transparent to approximately opaque for the designed dosage range. A mesh, grid or other target area 16 may be formed and have apertures 17 with a substantially higher or lower absorption value when compared with the remainder of the target area 16 so as to create a step function in the apparent intensity of radiation reaching the film packet 15 if the X-ray beam were to be essentially perfectly collimated. Blurring of the target image as recorded by the film packet 15 may be used to evaluate the scattering or other degradation of the X-ray beam.

FIG. 4 is a perspective view showing a typical dental X-ray device 30 positioned such that the X-ray device 30 is in contact with, or in close proximity to, the analyzer 1 as it would be with respect to a patient in taking an intraoral X-ray image. The spacing D between the dosimeter 10 and the position of the film packet 15 is determined so as to be comparable to the distance between the portion of the X-ray device in contact or close proximity to the patient skin and the film packet 15 being used in a patient environment. A typical dimension D may be about 1 inch (2.5 cm). The analyzer 1 is placed on a table or other support 70 so that the operator of the X-ray device can leave the immediate area in accordance with the usual procedure so as to avoid unintended personal X-ray exposure.

An X-ray exposure is made using a technique and exposure settings that may be chosen to replicate that used for a patient examination, or such other parameters as may be required by the testing instructions.

Figure 2B:
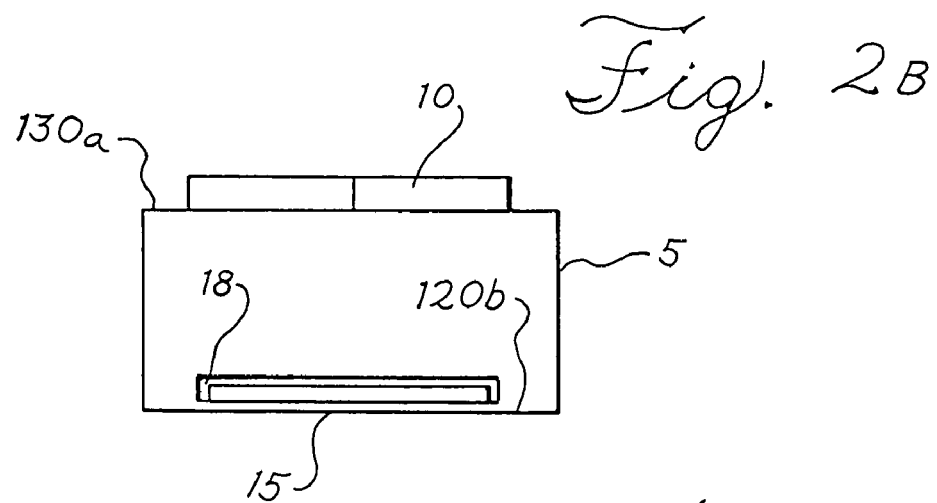
Figure 2C:
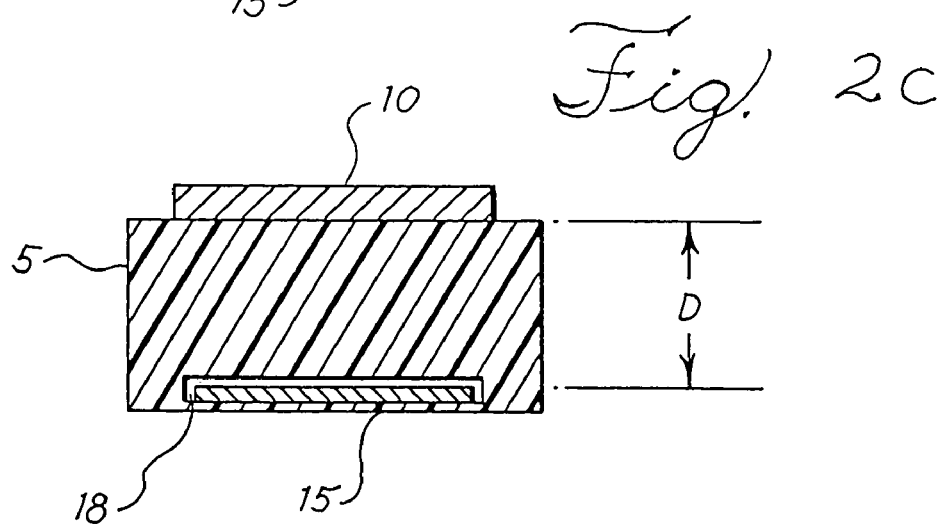

One or more X-ray film packets 15 or an image receptor may be adhered to the analyzer 1 as shown in FIG. 1, or inserted in the analyzer 1 as shown in FIG. 2, prior to the X-ray exposure, and thus the X-ray dose and an image of the X-ray test target may be obtained in a single exposure and with the same dose. In addition, a single packet may contain two or more films of different speeds or characteristics may be adhered to the analyzer 1. The use of two or more films having different speeds increases the dynamic range of the image data which can be obtained. Dental facilities may use one of at least two different film speeds (sensitivities) and the provision of a film package with multiple speeds for use in the analyzer enables the same analyzer to be sent to a dental facility without first ascertaining the speed of the film used. Such a multiple film package was obtained by special order from Kodak (Rochester, N.Y.). One or more of the film packets 15 may be developed at the facility using the same equipment and procedures as is used for actual patient X-rays. Alternatively, one or more of the film packets 15, or the entire analyzer 1 may be packaged in a protective container, which may be a lead foil pouch, and be sent for evaluation. The evaluation may include determining the X-ray dose from the dosimeter 10 and the image quality by evaluating one or more of the film packets 15 or other image receptor that are developed either at the X-ray facility or the evaluation facility.

The X-ray film may be a photographic type such as is available from the Eastman Kodak Company (Rochester, N.Y.). Several different speeds of film are available, and the dosage and the film development process may differ. When performing the survey test, the manufacturer, model number, and indicated radiation dosage (for example, beam current and time) may be recorded on the test form, and the film type and film development parameters may also be recorded. Each of the analyzers 1 may be provided with an individual serial number. Some of the information on the test form may be prerecorded on the test form. The operator would verify the information during the course of performing the test, and correct, modify, or supplement the information as necessary.

Figure 5A:
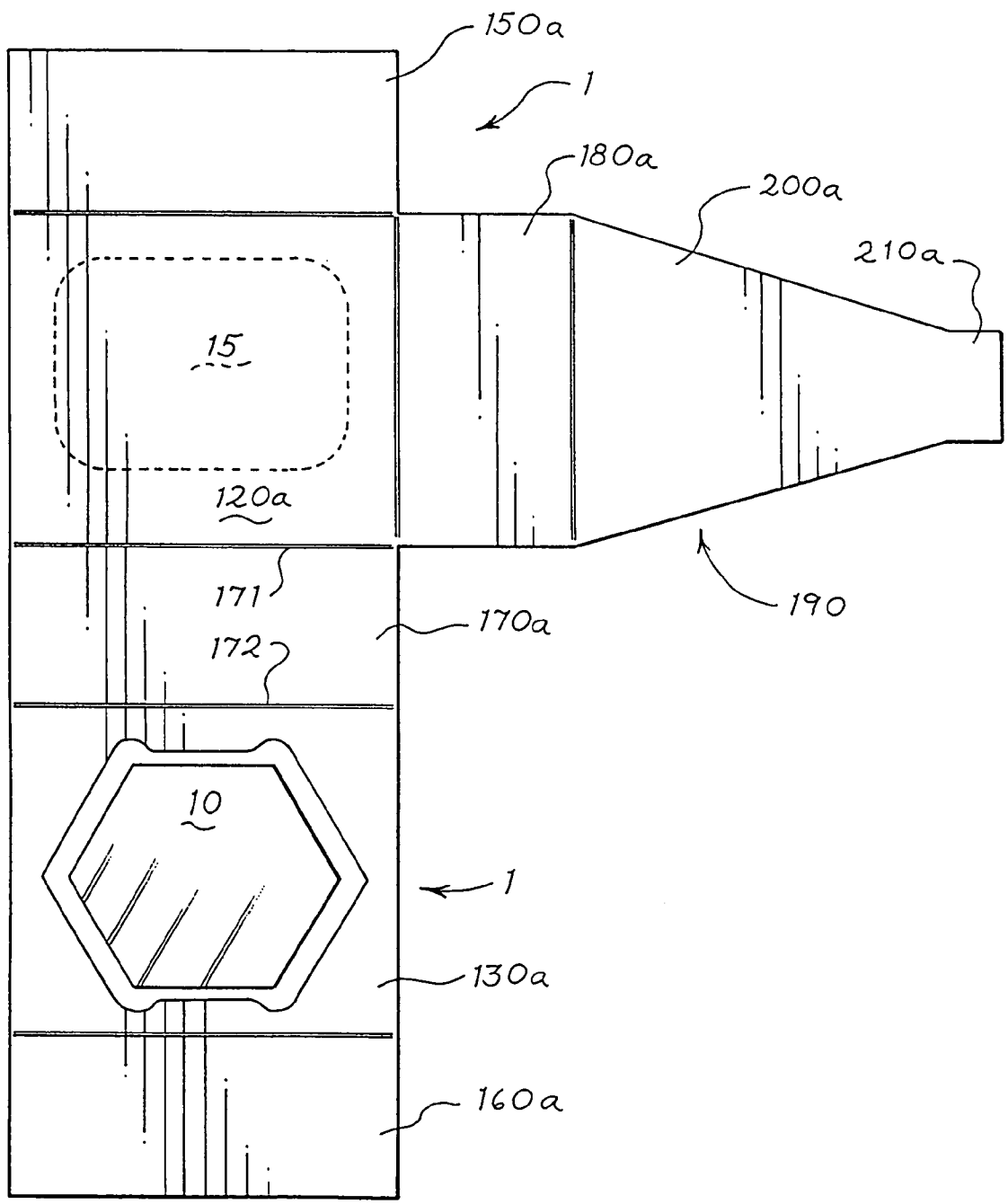
FIG. 5 shows: (A) a foldable example of the example of FIG. 1 prior to final assembly, where foldable material is shown as a flat sheet with bending lines; and, (B) an assembled foldable example, where the dosimeter has been translated into approximately the plane of the film.

FIG. 5A shows a top view of a foldable-type analyzer 1, where the device is opened up so that the housing may be laid out flat for illustrative purposes. When assembled as a product, and oriented so that that the analyzer 1 may be exposed to the X-ray device 30, the configuration of FIG. 1 would result. Interior solid lines such as lines 171, 172 indicate score or folding lines. The housing material may be assembled by bending at each of the score lines, except for those associated with the tab 190. The tab 190 includes surfaces 180a, 200a and 210a. Each of the surfaces 120, 130, 150, 160 and 170 is bent at a right angle to the adjoining surface so as to form the hollow parallelepiped structure 5 shown in FIG. 1. To complete the structure, surfaces 160 and 150 are overlapped so that a single composite surface results. The contacting portions of surfaces 150 and 160 (for example an outer surface 160a and the surface on the invisible side of 150) may be secured by an adhesive. Alternatively a staple, heat sealing or other process of securely joining the two surfaces may be used.

Figure 5B:
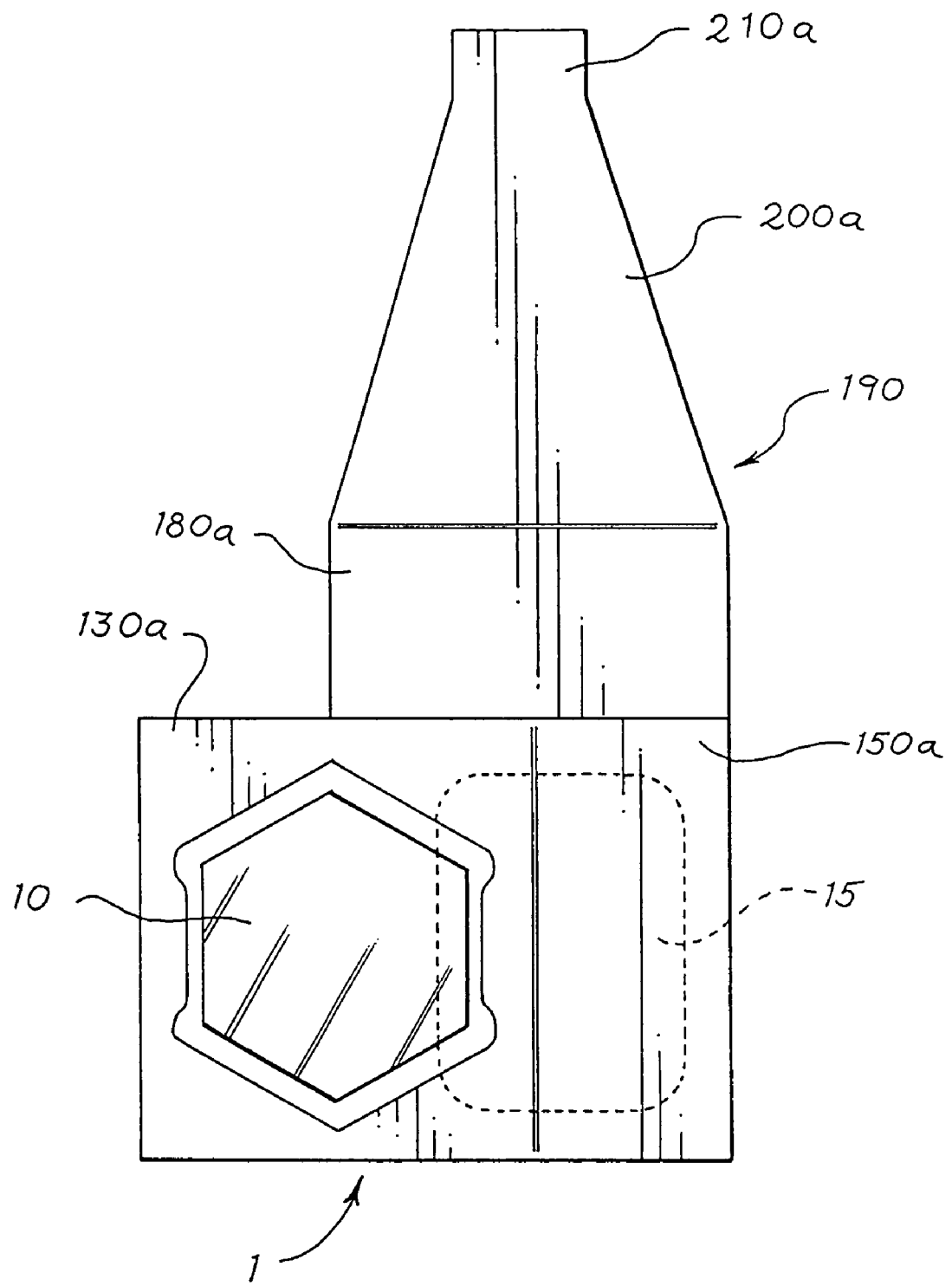

When assembled as described, the analyzer 1 may be collapsed so that the surfaces 130 and 120 are either in contact with each other or separated only by the thickness of an installed film packet 15 or other image receptor. This configuration, shown in a plan view in FIG. 5B may be suitable for shipping as it has a small height. When placed in use, the surfaces 130 and 120 may be moved so that they are at right angles to the sides 170 and the overlapped combination of 150 and 160, so as to form a hollow rectangular parallelepiped. In this state, the surface 180 may be bent at a right angle to the surface 120 and the surface 200 bent at an angle of somewhat greater that 90 degrees so that the a portion 200 of the tab 190 may be inserted into the opening formed in a proximal end of the hollow parallelepiped. In this state, the surface 180 fills a rectangular 7 opening in the holder 5, and stabilizes the holder 5 in the configuration of a hollow rectangular parallelepiped, as in FIG. 1. After use, the analyzer 1 may be returned to a folded configuration for shipment, by withdrawing the tab 190 from the interior of the housing 5 so that the configuration of FIG. 5B is realized. A person of ordinary skill in the art will recognize that the analyzer 1 may be assembled so that the tab 190 is attached either to the surface where the dosimeter 10 or the film packet 15 is affixed.

The film packet may either be placed in the analyzer 1 by the testing laboratory before shipment to the X-ray facility being surveyed, or the X-ray facility may place a film packet 15 in the device prior to exposure. Where the X-ray facility provides the film packet 15, an area with a sticky surface within a peripheral outline of the film packet 15 may be provided and covered by a plastic or other removable protective sheet (not shown). To use the analyzer 1, the protective sheet may be peeled off and the film packet 15 adhered to the film location. If a second film packet is used, the first film packet 15 may be pre-positioned, and the sticky area formed on an exposed to surface thereof, so that a second film packet 15 may be adhered to the first film packet. In this manner, a first film packet may be provided by the evaluation facility and a second film packet by the X-ray facility being tested. The second film packet may be a film packet developed locally by the X-ray facility being tested, and the first film packet may be developed at the testing facility.

The film packets may have differing photographic characteristics or speeds. Alternatively, only one film packet may be provided, and the place of development of the film specified by the test procedure. In another aspect, one film packet containing two different x-ray films with differing photographic characteristics or speeds may be provided. In a further alternative, the film packet or other image detector may be temporarily captivated by sliding the film packet into as slot or other retaining device as shown in FIG. 2.

Alternative imaging means are known or are being developed, which provide for electronic signal acquisition, rather than using photographic film. An example is the VisualiX eHD, which is available from GenDex Dental Systems (Milan, Italy) and which uses charge-coupled-device technology (CCD) where a cesium iodide scintillator is grown vertically on a carbon layer positioned over the CCD. The vertical growth process results in a columnar microstructure which guides the light produced by scintillation directly onto the CCD surface, both reducing light loss and providing for a high resolution. Such a device can produce an image that is directly transferable through an interface such as the universal serial bus (USB) to a personal computer, or the like, for display and analysis. Another alternative imaging device uses photostimulable phosphor (PSP) coated plates. Such a device is available as DenOptix QST from GenDex Dental Systems and is supplied in sizes that match those of traditional X-ray film. After exposure, the latent image is read using a laser scanning device and converted into a digital image. The image may be displayed on a computer monitor or projector, or printed for diagnosis or evaluation purposes. A PSP can be erased and reused. Thus, where the term image receptor, image detector, imaging means, or image detector means is used, film, a charge-coupled-device (CCD), photostimulable phosphor (PSP), or any other device or material now known or subsequently developed to temporarily or permanently detect X-rays so that an X-ray image may be recorded or recovered therefrom is intended. The use of any one of the imaging means herein is intended to include all other such imaging means, except where specifically excluded.

Positioning of the other imaging means may be done by adhering the devices to the same surface as a film packet or placing the imaging means in a side opening sized and dimensioned to receive the imaging means. As the form factor of the PSP may be similar to that of a film packet, the same holder as in FIGS. 1 or 2 may be used. In either instance, the film or PSP is read out or developed, as appropriate, and the resultant developed film or image sent to the evaluation facility with the exposed dosimeter 10. Where the form factor of the imaging modality is not that of the film packet or PSP device, such as with VisualiX eHD, a special adapter may be used to hold the imaging means in a suitable position.

Any suitable X-ray dosimeter 10 may be used. In an aspect, the dosimeter may use optically stimulated luminescence (OSL) technology packaged similarly to a radiation badge worn by personnel. OSL may use an $Al_2O_3$ crystalline material as the detector. The detector material is sandwiched within a multi-element filter pack and heat sealed within a laminated light-tight paper wrapper. Radiation exposure is measured by stimulating the $Al_2O_3$ material with selected wavelengths of laser or LED light causing it to luminesce in proportion to the amount of radiation exposure. The luminescence measured is applied to a dose algorithm that relies on the response ratios. The $Al_2O_3$ detector may be re-stimulated numerous times to confirm the accuracy of a radiation dose measurement. An example of this type of detector is available from Landauer, Inc. (Glenwood, Ill.) as the LUXEL+ dosimeter. The X-ray test target may be incorporated into the dosimeter, and positioned between the dosimeter detector and the imaging means, or it may be positioned above the dosimeter. The radiation detector material is not limited to $Al_2O_3$ Other radiation sensitive materials may be used including, but not limited to, thermoluminescent dosimeters (TLDs), MOSFETs (metal oxide semiconductor field effect transistors), photographic film, or other similar materials.

An exposure is made using the same technique as would be used for a dental X-ray: e.g., a dental intraoral or other type of dental radiograph. Subsequently, the analyzer 1 is removed from beneath the X-ray tube. If the film is to be processed locally, the film pack 15 is removed from the analyzer 1, and the film processed using the same equipment and techniques the facility customarily uses for photographic processing of patient films. The films, developed or undeveloped, and the dosimeter may returned via mail or courier to the supplier for analysis. In the example of digital imaging, the resulting digital images be returned to the supplier for analysis. The dose, as indicated by the dosimeter, may be evaluated by a dosimetry service provider and the results combined with the film or digital image analysis to provide a report.

An exposed film packet 15 which has been developed to show an X-ray image or radiograph is shown in FIG. 6. One or more circular areas 51-53 corresponding to differing X-ray absorption characteristics of the target areas 14*a*-*c* (the image of the third of the areas 53, is almost black in this radiograph), and a mesh or other pattern 54 corresponding the area 16 of the target are imaged onto the image receptor. The areas of differing X-ray absorption 51-53 are used to determine the quality of digital images or the appropriateness of film processing, the overall film density, the contrast (amount of density difference between different areas of the film) of the image, and the fog level of the film (photographic density where there should be none). The mesh pattern 54 may provide information regarding the sharpness of the dental radiograph. An embedded numeral 55 may be used to assist in tracking the individual film pieces. Any number of filters and x-ray test patterns of any types of materials may be added to provide additional information and refine the available information. Materials may include, but are not limited to, aluminum, copper, plastic, lead, or combinations of material such as an aluminum-copper sandwich. The materials are selected based on their spectral absorption characteristics and total radiation transmission.

The X-ray test target may be disposed inside of the dosimeter package, and may positioned above, and separated from, the OSL material. In the present example, the LUXEL+ product was used, due to cost and availability considerations, but any assembly performing the same or similar function may be used.

Various image processing techniques may be used to evaluate the images obtained by the film packs, or the other image detector means. The images from the film packs may be scanned into a computer by a conventional scanner, or one specifically adapted for scanning film transparencies. Images obtained using other image detector means may typically be in some type of digital format, and may be input into the analysis computer by means of removable media such as diskette, CR-ROM, DVD, or the like, by a digital interface such as the Universal Serial Bus (USB), or by transmission over a network, which may be the Internet or the like. Where transmission is by digital signals, the signals may be modulated on a carrier wave for at least a portion of the transmission path. Alternatively, images displayed by a computer may be printed by a printer interfaced to the computer storing the images.

The quality of an image may be determined by a variety of image analysis tools. In an aspect, a Fourier transform, which may be a fast Fourier transform (FFT), of the image of the mesh pattern may be used. After the Fourier transform has been computed, the area under the transform is determined. As the image becomes more blurred, the higher frequency spatial components of the mesh pattern are lost, and the area under the transform decreases. This may provide a quantitative measure of image quality.

Examples of film images used for evaluation are shown in FIG. 7. The images were obtained from two different X-ray units. The circular areas appear very similar in both of the images; however the mesh pattern is less sharp (more blurred or diffuse) in the bottom image. This indicates that the second X-ray unit is producing images with less sharpness, which would make it more difficult to see small details important to dental diagnosis. While the comparison made here is qualitative, a person of skill in the art will appreciate that a digital image may be quantitatively analyzed for gray scale values, and the sharpness of the transition between the holes (dark circles) and the remainder of the mesh may be ascertained. This measurement may be made for a plurality of transitions, and for the outer edge of the mesh portion of the target, and the results either averaged, or used individually, to evaluate the sharpness of the image. Similarly, the circular areas formed by the differing density materials of the target may be analyzed quantitatively in terms of grey scale.

Several aspects of the quality of the dental image and the radiation dose may be analyzed, which may include one or more of:

Image sharpness—for example, on a scale of 1 to 10, taking into account the effect of focal spot size and distribution, and imaging geometry on image sharpness;

Film contrast—density difference;

Film density—overall density;

Film base-plus-fog level—film density where none should be present;

Film speed—based on film density and dose;

Photographic processor quality—based on film contrast and density, and dose;

Digital image quality;

Dose—dose used to produce typical intraoral or other dental images; and

Half-value layer—dependent upon kVp and beam filtration.

Since the images may be analyzed by computer algorithms used in image processing, a procedure may be established so that the analysis is done with minimal subjectivity, reducing the variability in the results and increasing confidence in the validity of the outcome.

The analyzer 1 may be used in a method of performing an image quality and dose survey for dental facilities. Several aspects of the quality of the dental image and the radiation dose may be analyzed in performing the method, which may include one or more of determining:

Image sharpness—for example on a scale of 1 to 10, taking into account the effect of focal spot size and distribution, and imaging geometry on image sharpness;

Film contrast—density difference;

Film density—overall density;

Film base-plus-fog level—film density where none should be present;

Film speed—based on film density and dose

Photographic processor quality—based on film contrast and density, and dose;

Digital image quality;

Dose—dose used to produce typical intra-oral or other dental images; and

Half-value layer—dependent upon kVp and beam filtration.

The results of the facility evaluation survey may be used in different ways, depending on the objectives of the evaluation program. The results may be used to give counsel to the operators of the X-ray equipment so as to assist in identifying areas of improvement in technique or image quality, to determine if the device is operating properly or is a radiation hazard, or the like. In some instances, the report would be of an advisory nature, while in other situations, the report may prescribe a required course of action. For example, each of the aspects analyzed may be reported and accompanied by a histogram showing a distribution of test results with respect to a historical database of test results for other comparable facilities within a commensurable test group.

In an aspect, a method of evaluating facility quality may include the steps of: mailing a letter to dental facility from, for example, a state department of health official, indicating that a survey of the facility will be conducted; mailing dental image quality and dose analyzers, instructions for use, and a survey questionnaire to dental facilities; providing a toll-free phone number or web site to answer questions and provide any assistance needed by the dental practitioners and their staff in using the dental image quality and dose analyzers; receiving returning dosimeters, processed or unprocessed dental films or images, and questionnaire information from dental facilities; developing film images, if required, or inputting or digitizing digital dental images to a analysis device, which may be a computer operating in accordance with stored program instructions; reading and analyzing image quality and dosimeter information to determine patient dose and radiation beam quality (e.g., half-value layer—HVL); determining whether a specific dental X-ray unit has "Passed" or "Failed" the survey based on a comparison between pre-established metrics and the data determined from the analyzer. The pass-fail criteria will usually be established by a regulatory agency, committee or authority and may vary by political subdivision, such as a state or country. In addition, an Internet web site may be provided for the purpose of assisting dental staff in improving image quality and reducing patient and staff doses, and to answer questions about such issues.

The survey may also be used for determining the quality of dental images produced by new equipment upon installation, confirming the quality of images after equipment maintenance, or changes of major components, e.g., the X-ray tube; providing a summary report for a facility regarding image quality metrics and whether a specific dental x-ray unit "Passed" or "Failed" the test for each metric, and whether or not the facility "Passed" or "Failed" the survey; providing individual reports to each dental facility or regulatory agency; and, maintaining database of testing results.

The data base of results may be a historical record maintained for the individual facility, or may be a composite data base for a group of facilities having commensurable data.

Another example of the method may include the steps of: maintaining a data base of X-ray facilities; scheduling a periodic survey of the facilities; sending a dental image quality and dose analyzer and survey questionnaire to facility to be surveyed; receiving an exposed dental image quality and dose analyzer from the facility, including a completed questionnaire, and at least one of a developed or undeveloped exposed image receptor; determining the quality of the image by measuring the characteristics of the grey scale of areas of the image; and, preparing a report of the analysis of image quality.

In another aspect, the method may further include evaluating the radiation dose delivered to the dosimeter.

In another further aspect, the method may include constructing a data base of each registered X-ray facility and the details of the equipment installed therein, and the testing status thereof. Testing of the individual equipment at a facility may be scheduled in accordance with regulation, or law, or on a basis selected by the operator of the facility, and a dental image quality and dose analyzer sent to the facility for each of the equipment in the data base at the scheduled time. The analyzers may be uniquely serialized with a number recorded in the data base. A questionnaire may accompany the analyzer, and include identifying information for the equipment to be tested, and provide a place for recording information on the detailed parameters of test performed. Upon receipt of an exposed dental quality and dose analyzer, the dosimeter is evaluated to determine the exposure and HVL, and the film or other image data is evaluated to determine the image quality. The image quality may be characterized into aspects related to the quality of the radiation beam of the X-ray device, and aspects related to the quality of the subsequent image processing, such as the development of the film to produce a radiograph. The resultant information characterizing the results of the test may be entered into the data base. The test results may be compared with pre-established metrics that establish "Pass" and "Fail" criteria. The test results may be compared with a historical data base of commensurable test results for the specific facility or a group of facilities, and the test data may be added to the historical data base. A report of the test results and at least one of a "Pass-Fail" report or a comparison with historical data report may be produced and sent to the tested facility or regulatory agency. In the event that an exposed analyzer has not been received within a pre-determined time, follow-up action may be initiated.

In yet another aspect, the method may include the steps of: receiving a dental image quality and dose analyzer from an evaluation laboratory or regulatory agency; exposing the analyzer in accordance with the testing instructions; optionally, developing the film or obtaining an image of the X-ray test target; sending the exposed analyzer and the image or the image receptor to the evaluation laboratory or regulatory agency.

In still another aspect, the dental image quality and dose analyzer and method may be used for other types of X-ray devices and applications. For example, an equipment sales company may have the need to confirm for the purchaser that the equipment operates with quality and dose that meets state or national standards after servicing, installation or replacement of major components.

In a further aspect, a qualified person may visit a facility to expose the analyzer using the X-ray equipment at the facility and process the film using the facility photographic processing system. The dosimeter and processed films, or digital image, would then be sent for analysis.

Another method of determining X-ray machine image quality and dose, includes: forming a data base stored in a computer readable data format, the data base including: facility identifying information, including the type and identifying information for X-ray machines at the facility; test results for each X-ray machine; date of last test for each X-ray machine. A test date may be scheduled for each X-ray machine and a dental image quality and dose analyzer sent to the facility in accordance with the test schedule. When the analyzer has been returned and evaluated, the radiation dose and image quality parameters determined from the dental image quality and dose analyzer may be into the data base. The radiation dose and image quality parameters may be compared with at least one of a plurality of pre-established pass-fail criteria or with a historical assembly of commensurable data.

Any of the methods described may transmit information and data to or from the analysis facility, or to or from the facility having the X-ray machine, by using a wide area network (WAN) such as the Internet, and the data may be processed by a computer executing instructions of a computer program stored in a digital memory device such as a disk, RAM, ROM or flash memory, or the like.

While the methods disclosed herein have been described and shown with reference to particular steps performed in a particular order, it will be understood that these steps may be combined, sub-divided, or reordered to form an equivalent method without departing from the teachings of the present invention. Accordingly, unless specifically indicated herein, the order and grouping of steps is not a limitation of the present invention.

Although the examples herein relate to dental X-ray equipment and facilities, the apparatus and methods are equally applicable to other X-ray equipment and facilities including those used for medical and industrial use. The dosages and image quality parameters would be adjusted to be suitable for each application, as would the evaluation criteria.

Although the present invention has been explained by way of the examples described above, it should be understood to the ordinary skilled person in the art that the invention is not limited to the examples, but rather that various changes or modifications thereof are possible without departing from the spirit of the invention. Accordingly, the scope of the invention shall be determined only by the appended claims and their equivalents.

What is claimed is:

1. A device for measuring the dose and image quality of an X-ray machine, comprising:
   a radiation dosimeter; and
   a target having an X-ray test pattern,
   wherein a portion of the device, spaced apart from the radiation dosimeter and the target, is sized and dimensioned to accept an image receptor.

2. The device of claim 1, wherein, in an operating state, the dosimeter and the target are positioned at a first distance and a second distance, respectively, from the portion.

3. The device of claim 2, wherein, in a non-operating state, the dosimeter and the target are positioned at a third distance and a fourth distance from the portion, and the third and fourth distances are substantially less than the first and second distances.

4. The device of claim 2, wherein the first and the second distances are substantially the same distance.

5. The device of claim 4, wherein the first distance is determined as approximately a distance between a skin surface of a patient and a position of the image receptor when the image receptor is configured for producing an intraoral radiograph.

6. The device of claim 4 wherein the first distance is approximately one (1) inch (2.5 cm).

7. The device of claim 1, wherein the image receptor is a photographic film.

8. The device of claim 1, wherein the image receptor produces a latent digital image when exposed to X-ray radiation.

9. The device of claim 1, wherein the image receptor is one of a charge-coupled device (CCD) or a photostimulable phosphor (PSP).

10. The device of claim 1, wherein the image receptor is an image detector means.

11. The device of claim 1, wherein the image receptor produces electrical signals suitable for recording by a computer.

12. The device of claim 11, wherein the image receptor is connected to the computer by a Universal Serial Bus (USB).

13. The device of claim 1, wherein the radiation dosimeter is mounted to an exterior surface of a foldable structure, so that the radiation dosimeter is translatable into substantially the same plane as the portion thereof.

14. The device of claim 13, wherein the foldable structure comprises a planar surface having a rectangular shape, the surface folded to form a parallelepiped, two first opposing surfaces of are the portion sized and dimensioned to accept one of the radiation dosimeter or film pack, and two second opposing surfaces are sized so have a dimension approximately equal to the second distance.

15. The device of claim 14, wherein one of the first surfaces has a tab extension having a width equal to that of the first surface and foldable such that a first portion of the tab has a dimension equal to the dimension of the second surface.

16. The device of claim 15, wherein the tab has a second portion extending from the distal end of the first portion and foldable such that the second portion is introduced into the void formed by inner surfaces of the parallelepiped.

17. The device of claim 15, wherein in an operating state, the tab portion is folded orthogonal to the first surfaces and a tongue of the tab is inserted into the space formed by the first surfaces, so that the first surfaces are separated by the dimension of the second surface.

18. The device of claim 1, wherein the radiation dosimeter has a sensing element made of X- radiation sensitive material.

19. The device of claim 18, where the sensing element is at least one of $Al_2O_3$, TLD, MOSFET, or photographic film.

20. The device of claim 1, wherein an adhesive is applied to the portion and covered by a removable sheet.

21. The device of claim 1, wherein the device is structure formed of a material substantially transparent to X-radiation and the portion is a slot formed therein, disposed parallel to a surface-where the radiation dosimeter is affixed, the slot being sized and dimensioned to accept the image receptor, such that a surface of the image receptor is accommodatabie when disposed parallel to, and at substantially a first distance from, the dosimeter.

22. The device of claim 1, wherein the target is a substantially planar structure having two or more X-ray densities.

23. The device of claim 22, wherein the target has one or more regular patterned regions having differing X-ray densities.

24. The device of claim 22, wherein the target has a region of a first X-ray density, having a plurality regions of a second X-ray density regularly disposed therein.

25. The device of claim 24, wherein one of the first or second X-ray density regions is substantially transparent to X-radiation.

26. The device of claim 1, wherein a film pack is removably affixed to the portion.

27. The device of claim 26, wherein the film pack comprises two or more films having differing sensitivity to X-radiation.

28. The device of claim 27, wherein the two films correspond to standard dental X-ray films having different sensitivities.

29. The device of claim 28, wherein the film pack contains the films in an integral package.

30. A method of determining X-ray machine image quality and dose, the method comprising:
   receiving a image quality and dose analyzer;
   positioning the analyzer with respect to an X-ray machine to be tested;
   exposing the analyzer to X-rays; and
   returning the analyzer to a testing laboratory,
   wherein the image quality and dose analyzer includes:
      a radiation dosimeter;
      a target having an X-ray test pattern, and
      wherein a portion of the analyzer, spaced apart from the radiation dosimeter and the target, is sized and dimensioned to accept placement of an image receptor.

31. The method of claim 30, further comprising affixing a film pack to the analyzer prior to the step of exposing.

32. The method of claim 31, further comprising removing the film pack from the analyzer and developing the film pack to form a radiograph.

33. The method of claim 30, wherein returning the analyzer includes returning at least one of a developed or undeveloped radiograph, or a digitally obtained image.

34. The method of claim 30, wherein an image obtained by exposing the analyzer is transmitted to the testing laboratory by transmission over a network.

35. A method of determining X-ray machine image quality and dose, the method comprising:
sending an image quality and dose analyzer to a facility having an X-ray machine to be evaluated;
receiving an exposed analyzer from the facility;
determining the dose received by the dosimeter; and
analyzing an image provided by exposing the analyzer,
wherein the image quality and dose analyzer includes:
a radiation dosimeter;
a target having an X-ray test pattern, and
wherein a portion of the analyzer, spaced apart from the radiation dosimeter and the target, is sized and dimensioned to accept placement of an image receptor.

36. The method of claim 35, further comprising determining a value of a half-value-layer (HVL) parameter.

37. The method of claim 35, wherein analyzing includes measuring a gray scale of portions of an image corresponding to X-ray absorbing structures in the analyzer.

38. The method of claim 36, wherein the gray-scale measurements are used to determine image quality.

39. The method of claim 37, wherein the gray-scale measurements are used to determine X-ray beam quality.

40. The method of claim 25, wherein the beam quality is determined by a rate-of-change of gray scale of the image at step changes in the target X-ray density.

41. The method of claim 38, wherein the beam quality is determined by computing a Fourier transform of a gray scale of the image and determining the area under the transform.

42. The method of claim 35, wherein the step of receiving further includes receiving the image over a network.

43. The method of claim 42, wherein the received image data is stored in a computer data base.

44. The method of claim 35, wherein the image and analysis data from individual test is stored in a data base, the data being associated with the individual equipment being tested.

45. The method of claim 44, wherein data from individual tests having commensurable properties is aggregated in a historical test data base.

46. The method of claim 35, wherein the determined dose and the analyzed image quality are compared with pre-established criteria and a report is produced and sent to at least one of the facility or regulatory agency.

47. The method of claim 46, wherein the value of a half-value-layer (HVL) parameter is compared with established criteria.

48. A method of determining X-ray machine image quality and dose, the method comprising:
forming a data base stored in a computer readable data format, the data base including:
facility identifying information, including identifying information for X-ray machines at the facility;
test results for each X-ray machine;
date of last test for each X-ray machine;
scheduling a test for each X-ray machine;
sending a dental image quality and dose analyzer to the facility in accordance with the test schedule;
entering the radiation dose and image quality parameters determined from the dental image quality and dose analyzer into the data base; and
comparing the radiation dose and image quality parameters with at least one of a plurality of pre-established pass-fail criteria or with a historical assembly of commensurable data,
wherein the image quality and dose analyzer includes:
a radiation dosimeter;
a target having an X-ray test pattern, and
wherein a portion of the analyzer, spaced apart from the radiation dosimeter and the target, is sized and dimensioned to accept placement of an image receptor.

49. The method of claim 48, further including the step of preparing a report of test result parameters and sending the report to the facility.

50. The method of claim 48, further including adding the test result parameters to the commensurable historical data base.

* * * * *

UNITED STATES PATENT AND TRADEMARK OFFICE
CERTIFICATE OF CORRECTION

PATENT NO. : 7,503,694 B2 Page 1 of 1
APPLICATION NO. : 11/699858
DATED : March 17, 2009
INVENTOR(S) : Joel E. Gray It is certified that error appears in the above-identified patent and that said Letters Patent is hereby corrected as shown below:

In the Claims

Column 11, claim 14, line 66, before "are the portion sized" delete "of".

Column 12, claim 14, line 1, after "surfaces are sized" delete "so" and substitute --to-- in its place.

Column 12, claim 21, line 25, before "the radiation dosimeter" delete "surface-where" and substitute --surface where-- in its place; line 27, after "receptor is" delete "accommodatabie" and substitute --accommodatable-- in its place.

Column 12, claim 30, line 54, before "image quality and dose" delete "a" and substitute --an-- in its place.

Signed and Sealed this

Fourteenth Day of July, 2009

JOHN DOLL
*Acting Director of the United States Patent and Trademark Office*